(12) United States Patent
Nishi

(10) Patent No.: US 6,319,282 B1
(45) Date of Patent: Nov. 20, 2001

(54) CAPSULAR EQUATORIAL RING

(75) Inventor: Okihiro Nishi, Katano (JP)

(73) Assignee: Morcher GmbH (DE)

( * ) Notice: Subject to any disclaimer, the term of this patent is extended or adjusted under 35 U.S.C. 154(b) by 0 days.

(21) Appl. No.: 09/088,102

(22) Filed: Jun. 1, 1998

(30) Foreign Application Priority Data

Jun. 9, 1997 (DE) .............................. 197 24 108

(51) Int. Cl.$^7$ .................. A61F 2/16; A61F 2/14
(52) U.S. Cl. ............................. 623/6.39; 623/4.1
(58) Field of Search .................. 623/4, 6, 5.12, 623/6.38, 6.39, 4.1, 6.45, 6.49, 6.51, 6.55

(56) References Cited

U.S. PATENT DOCUMENTS

| | | | |
|---|---|---|---|
| 4,363,143 | * 12/1982 | Callahan | 623/6.43 |
| 4,476,591 | * 10/1984 | Arnott | 623/6.42 |
| 4,494,254 | * 1/1985 | Lopez | 623/6.42 |
| 4,711,638 | * 12/1987 | Lindstrom | 623/6 |
| 5,078,740 | * 1/1992 | Walman | 623/6.49 |
| 5,275,624 | * 1/1994 | Hara et al. | 623/4 X |
| 5,628,795 | 5/1997 | Langerman . | |
| 5,843,184 | * 12/1998 | Cionni | 623/4 |
| 5,968,094 | * 10/1999 | Werblin et al. | 623/6 |

FOREIGN PATENT DOCUMENTS

| | | |
|---|---|---|
| 0 478 929 | 8/1991 | (EP) . |
| 0 507 292 | 4/1992 | (EP) . |
| 2754173 | 4/1998 | (FR) . |

OTHER PUBLICATIONS

Mark's Standard Handbook for Mechanical Engineers Baumeister et al. 1979 Chapter 6 p. 161.*

* cited by examiner

Primary Examiner—Bruce Snow
Assistant Examiner—Brian Pellegrino
(74) Attorney, Agent, or Firm—D. Peter Hochberg; Katherine R. Vieyra; William H. Holt

(57) ABSTRACT

After surgical removal of the natural lens, a capsular equatorial ring may be implanted in the opened capsular bag of the eye in order to extend radially the equator of the capsular bag. Surprisingly, with a sharp edged formation of the junctions between the outer circumference and end faces of the ring, or with an axially wide outer circumferential surface, the probability of postoperative migrations of subcapsular epithelium cells on the capsular bag is significantly reduced.

2 Claims, 2 Drawing Sheets

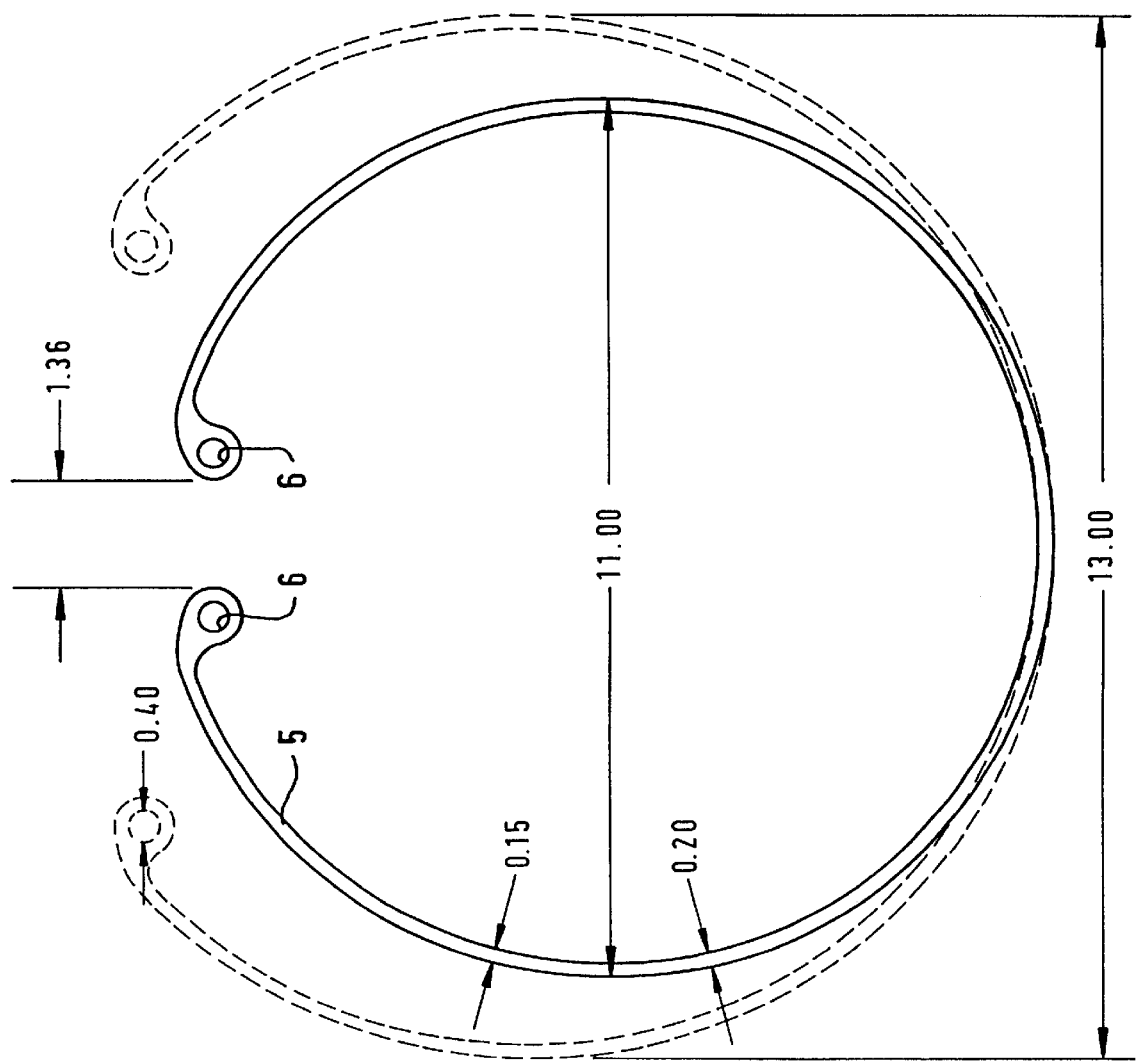

CAPSULAR EQUATORIAL RING

BACKGROUND OF THE INVENTION

1. Field of the Invention

The invention relates to a capsular equatorial ring which can be implanted into the opened capsular bag of an eye and, in the implanted state, bears with its outer circumference against the inside of the capsular bag at the equator of the latter and radially stabilizes the capsular bag, the said ring having a substantially cylindrical outer circumference adjoining with a relatively sharp edge the end faces of the ring.

2. Description of the Related Art

If the natural lens of an eye must be surgically removed, for example on account of a pronounced dullness, the capsular bag which receives the natural lens and is opened on the anterior side, facing the iris, for removal of the natural lens, is to be preserved in order to change the anatomical conditions in the eye as little as possible and to facilitate the implantation of an artificial intraocular lens.

However, the removal of the natural lens must be expected to entail more or less extensive damage to muscle of fibre bundles which secure the capsular bag externally in the region of its equator within the eye. In order to avoid the associated deformations of the capsular bag or excessive strain on the muscle fibres or tissue fibres remaining undamaged, it is known to implant in the opened capsular bag a capsular equatorial ring of the type specified at the beginning.

Such stabilizing elements are known, for example, from EP 0 507 292 A1. According to a first embodiment, in this case the capsular equatorial ring may be designed as a closed, foldable ring, with the result that the ring can, in spite of its closed form, be inserted into the capsular bag through relatively small surgical openings on the eye. For a good fit, the size of the capsular equatorial ring should, however, be adapted as precisely as possible to the capsular bag.

According to a second embodiment, the capsular equatorial ring may also be designed according to EP 0 507 292 A1 as an open ring part with ends which can be inserted into each other, in order to permit an adaptation to the equatorial circumference of the respective capsular bag.

It is known from EP 0 478 929 A1 to form at the ends to be connected to each other of an open capsular equatorial ring mating sawtooth profiles, in order to permit a connection which is particularly capable of bearing loads.

According to U.S. Pat. No. 5,628,795, the capsular bag rings are preferably to have a toroidal outside, it also being possible, if appropriate, for a ring form open in the shape of a C to be provided.

BRIEF SUMMARY OF THE INVENTION

The object of the invention is to provide a capsular equatorial ring with which the probability of postoperative migrations of the subcapsular epithelium cells on the capsular bag is particularly low.

This object is surprisingly achieved with a capsular equatorial ring of the type specified at the beginning if this ring is designed as an elastic spring clip which is open in the shape of a C and has inwardly bent-away ends which, in the implanted state of the capsular equatorial ring, are brought close to each other counter to spring resistance in such a way that, in the implanted state, the capsular equatorial ring attempts to open out.

The invention is based on the general idea of providing a capsular equatorial ring which on the one hand is able, on account of its spring clip characteristics, to adapt itself readily to the size of the respective capsular bag and on the other hand comes to bear with notable tension against the equator of the capsular bag. In combination with the profile of the ring, which forms a relatively sharp ring edge on both sides of the equatorial plane of the capsular bag, linear zones of the capsular bag in the region of these edges are then exposed to particularly high surface pressures, which can be further increased if, according to a preferred embodiment of the invention, the width of the capsular equatorial ring is made large in the direction of the ring axis.

Why this brings about a significant inhibitory effect on the migration of the subcapsular epithelium cells has not so far been definitively explained. However, the buckling of the capsular bag at the ring edges brought about by the capsular equatorial ring according to the invention is substantial. This buckling leads to a discontinuity at the capsular bag, which prevents a proliferation of subcapsular epithelium cells on the guiding or supporting structure formed by the capsular bag. In any event, it has been found with in-vitro cultures of subcapsular epithelium cells that a migration of these cells on one vessel wall is stopped at angular or buckled junctions with an adjoining vessel wall.

The axial width of the capsular equatorial ring at the equator of the capsular bag is advantageous because, inter alia, the capsular equatorial ring is forced into a parallel position with respect to the equatorial plane and consequently leads to a uniform tension at the equatorial region of the capsular bag, similar to when the natural lens is present. In addition internal contact between anterior wall parts and posterior wall parts of the capsular bag at the equatorial region is prevented, with the result that no synechia can occur.

Moreover, the invention offers the advantage that an artificial intraocular lens to be implanted, in particular a "foldable" lens of soft material, can be implanted more easily in the optimum position, or "slips" of its own accord into the optimum position on account of its elasticity.

At the free ends of this spring clip or on the capsular equatorial ring there may be formed on its inside small eyelets, in order to be able to grasp and manipulate more easily the element or the ring during the implantation.

In the axial view of the spring clip, the pieces of the spring clip adjoining the free ends may have a reduced thickness in comparison with a middle, approximately semicircular piece, or may taper towards the free ends.

With regard to the preferred features of the invention, reference is made moreover to the claims and the following explanation of a particularly preferred embodiment, which is described on the basis of the drawing, in which:

BRIEF DESCRIPTION OF THE SEVERAL VIEWS OF THE DRAWINGS

FIG. 1 shows a plan view (axial view) of a capsular equatorial ring according to the invention, FIG. 2 shows a side view

DETAILED DESCRIPTION OF THE INVENTION

Figure 3:
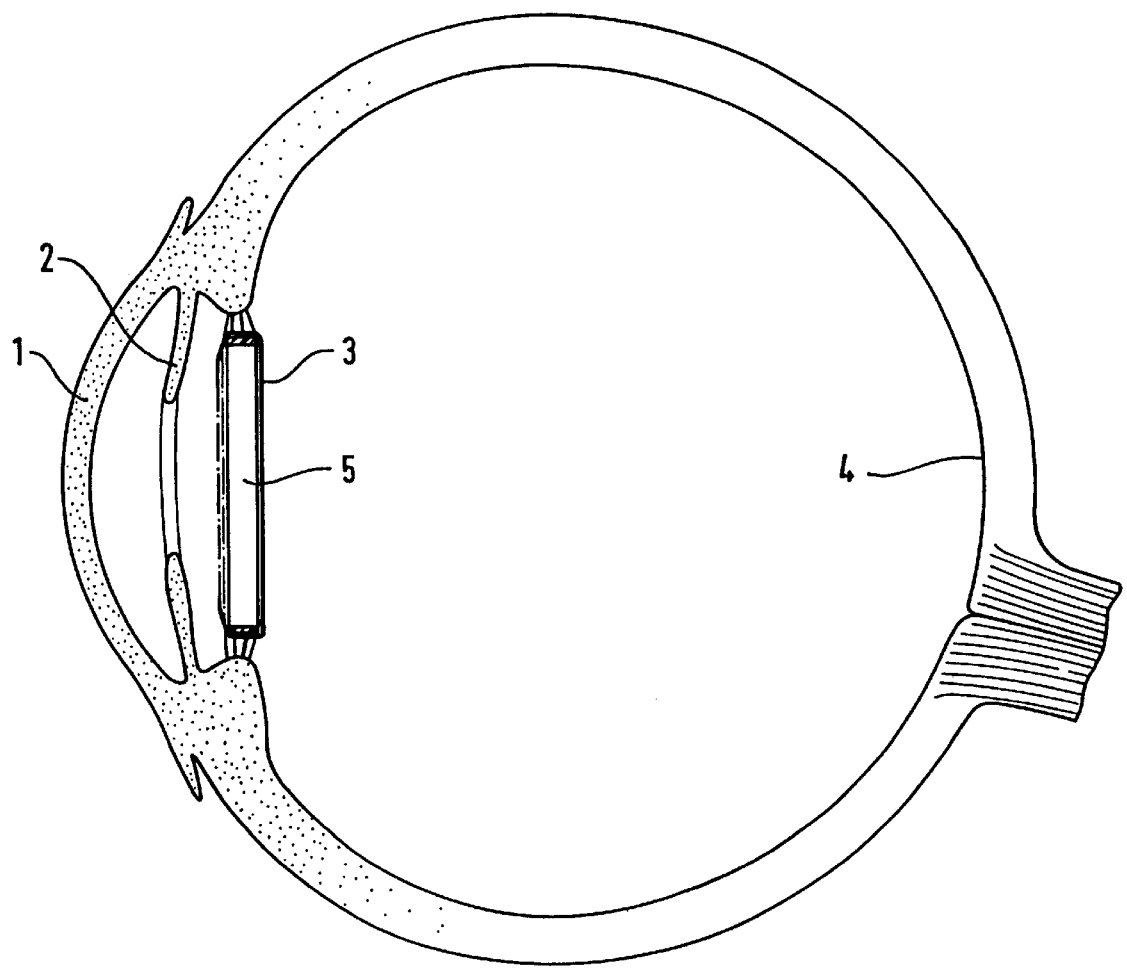
FIG. 3 shows a schematized longitudinal section of an eye with a capsular tensioning ring implanted in the opened capsular bag.

According to FIG. 3, the eye represented there has in a known way a cornea 1, an iris 2, a capsular bag 3, normally holding the natural lens, and a retina 4.

In the example represented, the natural lens has been removed. For this purpose the capsular bag 3 has been opened on its side facing the iris 2. In this operation, muscle fibres or tissue fibres which secure the capsular bag 3 at its equator within the eye are damaged to a greater or lesser extent.

In order to avoid associated deformations of the capsular bag 3 and overloading of the undamaged muscle fibres or tissue fibres, a capsular equatorial ring 5 may be inserted into the capsular bag 3.

According to FIGS. 1 and 2, the capsular equatorial ring 5 is designed as a ring part which is open in the shape of a C and consists of an elastically resilient plastic, for example PMMA (polymethyl methacrylate) or acrylic glass or some other material which is well tolerated, such as polycarbonate for example, optical material properties being of secondary significance.

In this case, the capsular equatorial ring 5 has a substantially rectangular cross-section, the long sides of the rectangle extending parallel to the ring axis and pronounced relatively sharp edges being formed between the outer circumference and the end faces of the ring 5.

The free C ends of the capsular equatorial ring 5 are bent away inwards and provided with formed-on small eyelets 6.

The ring segments adjoining the eyelets 6 and respectively forming approximately a quarter circle have a smaller radial thickness than an approximately semicircular middle ring segment, it being possible for the aforementioned ring segments to taper in the direction of the eyelets 6.

In FIG. 1, the state of the capsular equatorial ring 5 implanted in the capsular bag 3 is represented by solid lines. In this state, the capsular equatorial ring 5 resiliently attempts to open out. The relieved state of the capsule tensioning ring 5 is represented in FIG. 1 by dashed lines.

Also indicated in FIGS. 1 and 2 are preferred dimensions of the capsular equatorial ring, in mm in each case, deviations of ±0.05 mm being readily tolerable.

In principle, however, other dimensions may also be provided.

It is particular advantageous that the outer circumferential surface of the capsular equatorial ring 5 bearing against the inside of the capsular bag 3 has in the direction of the ring axis a comparatively large width, which is preferably about 5 to 7% of the diameter of the capsular equatorial ring 5 in the implanted state.

The capsular bag according to FIG. 3 is distinctly buckled at the ring edges between the outer circumference of the capsular equatorial ring 5 and its end faces.

What is claimed is:

1. A capsular equatorial ring being implantable in an opened capsular bag of an eye and against bearing against the inside of the capsular bag at the equator of the capsular bag for radially stabilizing the capsular bag, said ring being an elastically resilient C-shaped spring clip having a longitudinal axis, outer and inner circumferences and a substantially rectangular cross section having parallel long sides parallel to said longitudinal axis and short sides perpendicular to said long sides and having sharp edges with said long sides, said ring having a width in the direction of said longitudinal axis being greater than about 5% of the diameter of the implanted spring clip, said spring clip further having free ends with eyelets and ring segments adjoining the eyelets and tapering in the direction of said eyelets, said free ends being inwardly bent away in a radial direction of said spring clip, said free ends being movable towards each other to reduce the diameter of said spring clip for said implanting said spring clip in the opened capsular bag of the eye, said spring clip being movable towards its initial diameter upon being released in the capsular bag, and having a radial thickness in the middle region between the free ends of about 0.20±0.05 mm, and in the regions adjacent to the free ends.

2. A capsular equatorial ring being implantable in an opened capsular bag of an eye and bearing against the inside of the capsular bag at the equator of the capsular bag for radially stabilizing the capsular bag, said ring being an elastically resilient C-shaped spring clip having a longitudinal axis, outer and inner circumferences and a substantially rectangular cross section having parallel long sides parallel to said longitudinal axis and short sides perpendicular to said long sides and having sharp edges with said long sides, said ting having a width in the direction of said longitudinal axis being greater than about 5% of the diameter of the implanted spring clip, said spring clip further having free ends with eyelets and ring segments adjoining the eyelets and forming approximately a quarter circle between the walls of said eyelets and the inner circumference of said ring, said ring segments tapering in the direction of said eyelets, said quarter circle having a smaller radial thickness than an approximately semi-circular middle ring segment, said free ends being inwardly bent away in a radial direction of said spring clip, said free ends being movable towards each other to reduce the diameter of said spring clip for implanting said spring clip in the opened capsular bag of the eye, said spring clip being movable towards its initial diameter upon being released in the capsular bag.

\* \* \* \* \*